United States Patent [19]

Goldie et al.

[11] Patent Number: 4,990,341

[45] Date of Patent: * Feb. 5, 1991

[54] CONTROLLED RELEASE HYDROMORPHONE COMPOSITION

[75] Inventors: Robert S. Goldie, Comberton; Sandra T. A. Malkowska, Landbeach; Stewart T. Leslie, Cambridge, all of United Kingdom; Ronald B. Miller, Basel, Switzerland

[73] Assignee: Euroceltique, S.A., Luxembourg, Luxembourg

[*] Notice: The portion of the term of this patent subsequent to Jul. 4, 2006 has been disclaimed.

[21] Appl. No.: 345,354

[22] Filed: Apr. 28, 1989

Related U.S. Application Data

[63] Continuation of Ser. No. 113,865, Oct. 26, 1987, Pat. No. 4,844,909.

[30] Foreign Application Priority Data

Oct. 26, 1987 [GB] United Kingdom ................ 8626098

[51] Int. Cl.$^5$ ................................................ A61K 9/20
[52] U.S. Cl. .................... 424/484; 424/495; 424/496; 424/497; 424/498; 424/499; 424/501; 424/502
[58] Field of Search ............... 424/473, 495, 480, 498, 424/484, 488, 493, 496, 497, 499, 501, 502

[56] References Cited

U.S. PATENT DOCUMENTS

| | | | |
|---|---|---|---|
| 4,320,759 | 3/1982 | Theeuwes | 128/260 |
| 4,576,604 | 3/1986 | Guittard et al. | 604/890 |
| 4,599,342 | 7/1986 | LaHann | 514/282 |
| 4,622,218 | 11/1986 | Bodor | 424/9 |
| 4,806,341 | 2/1989 | Chien et al. | 424/449 X |

OTHER PUBLICATIONS

Chemical Abstracts, 108 (4):26895u.

*Primary Examiner*—Thurman K. Page
*Attorney, Agent, or Firm*—Steinberg & Raskin

[57] ABSTRACT

A solid controlled release, oral dosage form, the dosage form comprising a therapeutically effective amount of hydromorphone or a salt thereof in a matrix wherein the dissolution rate in vitro of the dosage form, when measured by the USP Paddle Method of 100 rpm in 900 ml aqueous buffer (pH between 1.6 and 7.2) at 37° C. is between 12.5% and 42.5% (by weight) hydromorphone released after 1 hour, between 25% and 55% (by weight) hydromorphone released after 2 hours, between 45% and 75% (by weight) hydromorphone released after 4 hours and between 55% and 85% (by weight) hydromorphone released after 6 hours, the in vitro release rate being independent of pH between pH 1.6 and 7.2 and chosen such that the peak plasma level of hydromorphone obtained in vivo occurs between 2 and 4 hours after administration of the dosage form.

6 Claims, No Drawings

CONTROLLED RELEASE HYDROMORPHONE COMPOSITION

This is a continuation of application Ser. No. 113,865, filed Oct. 26, 1987, now U.S. Pat. No. 4,844,909.

The present invention relates to a solid, controlled release, oral dosage form containing hydromorphone for use in the treatment of moderate to severe pain.

According to the present invention there is provided a solid, controlled release, oral dosage form, the dosage form comprising a therapeutically effective amount of hydromorphone or a salt thereof in a matrix wherein the dissolution rate in vitro of the dosage form, when measured by the USP Paddle Method at 100 rpm in 900 ml. aqueous buffer (pH between 1.6 and 7.2) at 37° C. is between 12.5 and 42.5% (by wt) hydromorphone released after 1 hour, between 25 and 55% (by wt) hydromorphone released after 2 hours, between 45 and 75% (by wt) hydromorphone released after 4 hours and between 55 and 85% (by wt) hydromorphone released after 6 hours, the in vitro release rate being independent of pH between pH 1.6 and 7.2 and such that the peak plasma level of hydromorphone obtained in vivo occurs between 2 and 4 hours after administration of the dosage form.

Preferably, the dosage form contains an analgesically effective amount of hydromorphone or a salt thereof.

USP Paddle Method is the Paddle Method described in US Pharmacopoeia XXI (1985).

In the present specification, "independent of pH" means that the difference, at any given time, between the amount of hydromorphone released at pH 1.6 and the amount released at any other pH up to, and including, pH 7.2 (when measured in vitro using the USP Paddle Method at 100 rpm in 900 ml aqueous buffer) is 10% (by weight) or less. The amounts released being, in all cases, a mean of at least three experiments.

In the present specification, "peak plasma level of hydromorphone obtained in vivo" refers to the maximum mean concentration of hydromorphone found in the plasma of at least six healthy volunteers, when (the volunteers are) subjected to a single dose, pharmacokinetic study.

Preferably the dissolution rate is between 17.5 and 37.5% (by wt) hydromorphone released after 1 hour, between 30 and 50% (by wt) after 2 hours, between 50 and 70% (by wt) after 4 hours and between 60 and 80% (by wt) after 6 hours. Most preferably, the dissolution rate is between 22.5 and 32.5% (by wt) hydromorphone released after 1 hour between 35 and 45% (by wt) after 2 hours, between 55 and 65% (by wt) after 4 hours and between 65 and 75% (by wt) after 6 hours.

Preferably the peak plasma level of hydromorphone is obtained in vivo between 2.25 and 3.75 hours after administration of the dosage form.

When the hydromorphone is administered as hydromorphone hydrochloride and the method of hydromorphone in plasma analysis is a double antibody radioimmunoassay (as hereinafter described), the peak plasma level of hydromorphone (per ml. of plasma) is preferably between $0.5 \times 10^{-6}$ and $2.0 \times 10^{-6}$, most preferably between $0.5 \times 10^{-6}$ and $1.5 \times 10^{-6}$, of the amount of hydromorphone hydrochloride administered orally.

Thus, if 4 mg of hydromorphone hydrochloride is administered, the peak plasma level of hydromorphone is preferably between 2 and 8 ngml$^{-1}$, especially between 2 and 6ngml$^{-1}$.

When hydromorphone base or a salt other than the hydrochloride is administered, the preferred ratio of drug administered to peak plasma level of hydromorphone must be adjusted according to the molecular weight of the base or salt.

By keeping within these narrow ranges for in vitro dissolution rates, the present inventors have surprisingly found that although the present oral dosage forms give peak plasma levels of hydromorphone between 2 and 4 hours after administration, they still afford therapeutic levels of hydromorphone in vivo over at least a 12 hour period, and may therefore be used on a twice daily basis.

In order to obtain a controlled release drug dosage form having at least a 12 hour therapeutic effect, it is usual in the pharmaceutical art to produce a formulation that gives a peak plasma level of the drug between about 4–8 hours after administration (in a single dose study). The present inventors have surprisingly found that, in the case of hydromorphone, a peak plasma level at between 2–4 hours after administration gives at least 12 hours pain relief and, most surprisingly, that the pain relief obtained with such a formulation is greater than that achieved with formulations giving peak plasma levels (of hydromorphone) in the normal period of 1–2 hours after administration.

Furthermore, in the case of the present dosage form, therapeutic levels are generally achieved without concurrent side effects, such as nausea, vomiting, constipation and drowsiness, which are often associated with high blood levels of hydromorphone. There is also evidence to suggest that the use of the present dosage forms leads to a reduced risk of drug addiction.

A further advantage of the present composition, which releases hydromorphone at a rate that is independent of pH between 1.6 and 7.2, is that it avoids dose dumping upon oral administration. In other words, the hydromorphone is released evenly throughout the gastrointestinal tract.

The present oral dosage form may be presented as, for example, granules, spheroids or pellets in a capsule or in any other suitable solid form. Preferably, however, the oral dosage form is a tablet.

The present oral dosage form preferably contains between 1 and 100 mg, especially between 2 and 50 mg, most especially between 2 and 40 mg, of hydromorphone hydrochloride. Alternatively the dosage form may contain molar equivalent amounts of other hydromorphone salts or of the hydromorphone base.

The present matrix may be any matrix that affords in vitro dissolution rates of hydromorphone within the narrow ranges required and that releases the hydromorphone in a pH independent manner. Preferably the matrix is a controlled release matrix, although normal release matrices having a coating that controls the release of the drug may be used. Suitable materials for inclusion in a controlled release matrix are (a) Hydrophilic polymers, such as gums, cellulose ethers, acrylic resins and protein derived materials. Of these polymers, the cellulose ethers, especially hydroxyalkylcelluloses and carboxyalkylcelluloses, are preferred. The oral dosage form may contain between 1% and 80% (by weight) of at least one hydrophilic or hydrophobic polymer.

(b) Digestible, long chain ($C_8$–$C_{50}$, especially $C_{12}$–$C_{40}$), substituted or unsubstituted hydrocarbons, such as fatty acids, fatty alcohols, glyceryl esters of fatty acids, mineral and vegetable oils and waxes. Hydrocarbons having a melting point of between 25° and 90° C. are preferred. Of these long chain hydrocarbon materials, fatty (aliphatic) alcohols are preferred. The oral dosage form may contain up to 60% (by weight) of at least one digestible, long chain hydrocarbon.

(c) Polyalkylene glycols. The oral dosage form may contain up to 60% (by weight) of at least one polyalkylene glycol.

One particularly suitable matrix comprises at least one water soluble hydroxyalkyl cellulose, at least one $C_{12}$–$C_{36}$, preferably $C_{14}$–$C_{22}$, aliphatic alcohol and, optionally, at least one polyalkylene glycol.

The at least one hydroxyalkyl cellulose is preferably a hydroxy ($C_1$ to $C_6$) alkyl cellulose, such as hydroxypropylcellulose, hydroxypropylmethylcellulose and, especially, hydroxyethyl cellulose. The amount of the at least one hydroxyalkyl cellulose in the present oral dosage form will be determined, inter alia, by the precise rate of hydromorphone release required. Preferably however, the oral dosage form contains between 5% and 25%, especially between 6.25% and 15% (by wt) of the at least one hydroxyalkyl cellulose.

The at least one aliphatic alcohol may be, for example, lauryl alcohol, myristyl alcohol or stearyl alcohol. In particularly preferred embodiments of the present oral dosage form, however, the at least one aliphatic alcohol is cetyl alcohol or cetostearyl alcohol. The amount of the at least one aliphatic alcohol in the present oral dosage form will be determined, as above, by the precise rate of hydromorphone release required. It will also depend on whether at least one polyalkylene glycol is present in or absent from the oral dosage form. In the absence of at least one polyalkylene glycol, the oral dosage form preferably contains between 20% and 50%, especially between 25% and 45% (by wt) of the at least one aliphatic alcohol. When at least one polyalkylene glycol is present in the oral dosage form, then the combined weight of the at least one aliphatic alcohol and the at least one polyalkylene glycol preferably constitutes between 20% and 50%, especially between 25% and 45% (by wt) of the total dosage form.

In the present preferred dosage form, the ratio of the at least one hydroxyalkyl cellulose to the at least one aliphatic alcohol/polyalkylene glycol determines, to a considerable extent, the release rate of the hydromorphone from the formulation. A ratio of the at least one hydroxyalkyl cellulose to the at least one aliphatic alcohol/polyalkylene glycol of between 1:2 and 1:4 is preferred, with a ratio of between 1:3 and 1:4 being particularly preferred.

The at least one polyalkylene glycol may be, for example, polypropylene glycol or, which is preferred, polyethylene glycol. The number average molecular weight of the at least one polyalkylene glycol is preferred between 1000 and 15000 especially between 1500 and 12000.

Another suitable controlled release matrix would comprise an alkylcellulose (especially ethyl cellulose), a $C_{12}$ to $C_{36}$ aliphatic alcohol and, optionally, a polyalkylene glycol.

In addition to the above ingredients, a controlled release matrix may also contain suitable quantities of other materials, e.g. diluents, lubricants, binders, granulating aids, colorants, flavorants and glidants that are conventional in the pharmaceutical art.

As an alternative to a controlled release matrix, the present matrix may be a normal release matrix having a coat that controls the release of the drug. In a particularly preferred embodiment of this aspect of the invention, the present dosage form comprises film coated spheroids containing active ingredient and a non-water soluble spheronising agent. The term spheroid is known in the pharmaceutical art and means a spherical granule having a diameter of between 0.5 mm and 2.5 mm, especially between 0.5 mm and 2 mm.

The spheronising agent may be any pharmaceutically acceptable material that, together with the active ingredient, can be spheronised to form spheroids. Microcrystalline cellulose is preferred.

A suitable microcrystalline cellulose is, for example, the material sold as Avicel PH 101 (Trade Mark, FMC Corporation). According to a preferred aspect of the present invention, the film coated spheroids contain between 70% and 99% (by wt), especially between 80% and 95% (by wt), of the spheronising agent, especially microcrystalline cellulose.

In addition to the active ingredient and spheronising agent, the spheroids may also contain a binder. Suitable binders, such as low viscosity, water soluble polymers, will be well known to those skilled in the pharmaceutical art. However, water soluble hydroxy lower alkyl celluloses, such as hydroxy propyl cellulose, are preferred. Additionally (or alternatively) the spheroids may contain a water insoluble polymer, especially an acrylic polymer, an acrylic copolymer, such as a methacrylic acid-ethyl acrylate copolymer, or ethyl cellulose.

The spheroids are film coated with a material that permits release of the hydromorphone (or salt) at a controlled rate in an aqueous medium. The film coat is chosen so as to achieve, in combination with the spheroids' other ingredients, the in-vitro release rate outlined above (between 12.5% and 42.5% (by wt) release after 1 hour, etc.).

The film coat will generally include a water insoluble material such as (a) a wax, either alone or in admixture with a fatty alcohol,
(b) shellac or zein,
(c) a water insoluble cellulose, especially ethyl cellulose,
(d) a polymethacrylate, especially Eudragit (Trade Mark).

Preferably, the film coat comprises a mixture of the water insoluble material and a water soluble material. The ratio of water insoluble to water soluble material is determined by, amongst other factors, the release rate required and the solubility characteristics of the materials selected.

The water soluble material may be, for example, polyvinylpyrrolidone or, which is preferred, a water soluble cellulose, especially hydroxypropylmethyl cellulose.

Suitable combinations of water insoluble and water soluble materials for the film coat include shellac and polyvinylpyrrolidone or, which is preferred, ethyl cellulose and hydroxypropylmethyl cellulose.

In order to facilitate the preparation of a solid, controlled release, oral dosage form according to this invention there is provided, in a further aspect of the present invention, a process for the preparation of a solid, controlled release, oral dosage form according to the present invention comprising incorporating hydromorphone or a salt thereof in a controlled release matrix. Incorporation in the matrix may be effected, for example, by (a) forming granules comprising at least one water soluble hydroxyalkyl cellulose and hydromorphone or a hydromorphone salt,
(b) mixing the hydroxyalkyl cellulose containing granules with at least one $C_{12}$–$C_{36}$ aliphatic alcohol, and
(c) optionally, compressing and shaping the granules.

Preferably, the granules are formed by wet granulating the hydroxyalkyl cellulose/hydromorphone with water. In a particularly preferred embodiment of this process, the amount of water added during the wet granulation step is preferably between 1.5 and 5 times, especially between 1.75 and 3.5 times, the dry weight of the hydroxyalkylcellulose.

The present solid, controlled release, oral dosage form may also be prepared, in the form of film coated spheroids, by
(a) blending a mixture comprising hydromorphone or a hydromorphone salt and a non-water soluble spheronising agent,
(b) extruding the blended mixture to give an extrudate,
(c) spheronising the extrudate until spheroids are formed, and
(d) coating the spheroids with a film coat.

The present solid, controlled release, oral dosage form and processes for its preparation will now be described by way of example only.

EXAMPLE 1

Hydromorphone hydrochloride (4.0 gm) was wet granulated with lactose monohydrate (167.0 gm) and hydroxyethyl cellulose (40.0 gm., Natrosol 250 HX, Trade Mark) and the granules were sieved through a 12 mesh screen. The granules were then dried in a Fluid Bed Dryer at 50° C. and passed through a 16 mesh screen.

To the warmed hydromorphone containing granules was added molten cetostearyl alcohol (120.0 gm) and the whole was mixed thoroughly. The mixture was allowed to cool in the air, regranulated and sieved through a 16 mesh screen.

Purified Talc (6.0 gm) and magnesium stearate (3.0 gm) were then added and mixed with the granules. The granules were then compressed into 1000 tablets each containing,

|  | mg/tablet |
| --- | --- |
| Hydromorphone Hydrochloride | 4.0 |
| Lactose Monohydrate | 167.0 |
| Hydroxyethylcellulose | 40.0 |
| Cetostearyl alcohol | 120.0 |
| Purified Talc | 6.0 |
| Magnesium stearate | 3.0 |

EXAMPLE 2

The procedure of Example 1 was followed, but with reduced quantities of cellulose and fatty alcohol, to give 1000 tablets each containing,

|  | mg/tablet |
| --- | --- |
| Hydromorphone Hydrochloride | 4.0 |
| Anhydrous Lactose | 167.0 |
| Hydroxyethylcellulose | 30.0 |
| Cetostearyl Alcohol | 90.0 |
| Purified Talc | 6.0 |
| Magnesium Stearate | 3.0 |

EXAMPLE 3

Hydromorphone hydrochloride (4.0 gm) was wet granulated with lactose monohydrate (30.0 gm) hydroxyethyl cellulose (10.0 gm; Natrosol 250 HX, Trade Mark) and methacrylic acid copolymer (3.0 gm, Eudragit L-100-55., Trade Mark) and the granules were sieved through a 12 mesh screen. The granules were then dried in a Fluid Bed Dryer at 50° C. and passed through a 16 mesh screen.

To the warmed hydromorphone containing granules was added molten cetostearyl alcohol (30.0 gm) and the whole was mixed thoroughly. The mixture was allowed to cool in the air, regranulated and sieved through a 16 mesh screen.

The granules were then compressed into 1000 tablets each containing,

|  | mg/tablet |
| --- | --- |
| Hydromorphone Hydrochloride | 4.0 |
| Lactose Monohydrate | 30.0 |
| Hydroxyethylcellulose | 10.0 |
| Methacrylic Acid Copolymer | 30.0 |
| Cetostearyl alcohol | 30.0 |

EXAMPLE 4

Hydromorphone hydrochloride (50 g) microcrystalline cellulose (Avicel PHI01, 440 g) and hydroxypropylmethyl cellulose (Methocel E15, 10 g) were dry mixed. Water (350 ml) was then added and the mixture was granulated. The granulated mass was extruded through a 1 mm cylinder and the extrudate was spheronised. The resultant spheroids were dried at 60° C. in a fluid bed drier. The moisture content of the dried spheroids was found to be 4.3% w/w (Karl-Fischer). The dried spheroids were then sieved and the sieve fraction between 1.0 mm and 1.4 mm was retained.

The spheroids were coated with a film coat, having the formulation given below, to a level of 15% w/w.

Film Coat Formulation

| Ethylcellulose N10 | 4.0% w/v |
| --- | --- |
| Hydroxypropylmethylcellulose (Methocel E15) | 1.0% w/v |
| Propylene glycol BP | 0.5% w/v |
| Opaspray K-1-4132 | 3.0% w/v |
| Methanol | 60.0% v/v |
| Dichloromethane | to 100.0% v/v |

Vitro Dissolution Studies

In vitro dissolution studies were conducted on tablets prepared as described in Example 1. The dissolution method was the USP Paddle Method described in US Pharmacopoeia XXI (1985). The paddle speed was 100 rpm, the temperature was 37° C. and the medium was 900 ml water. Results are given in Table 1.

TABLE 1

| Time (hr) | wt. % Hydromorphone released |
| --- | --- |
| 1 | 28.3 |

TABLE 1-continued

| Time (hr) | wt. % Hydromorphone released |
|---|---|
| 2 | 41.8 |
| 3 | 51.5 |
| 4 | 59.5 |
| 5 | 65.5 |
| 6 | 70.0 |
| 7 | 75.0 |
| 8 | 80.0 |

In vitro dissolution studies were conducted on tablets prepared as described in Example 2. The dissolution method was the USP Paddle Method described in US Pharmacopoeia XXI (1985). The paddle speed was 100 rpm, the temperature was 37° C. and the medium was an aqueous buffer (pH 6.5).

Results are given in Table 2.

TABLE 2

| Time (hr) | wt. % Hydromorphone released |
|---|---|
| 1 | 26 |
| 2 | 41 |
| 3 | 52 |
| 4 | 60 |
| 5 | 67 |
| 6 | 74 |
| 7 | 79 |
| 8 | 83 |

In vitro dissolution studies were conducted on tablets prepared as described in Example 3. The dissolution method was the USP Paddle Method described in US Pharmacopoeia XXI (1985). The paddle speed was 100 rpm, the temperature was 37° C. and the medium was 900 ml water.

Results are given in Table 3.

TABLE 3

| Time (hr) | wt. % Hydromorphone released |
|---|---|
| 1 | 35 |
| 2 | 50 |
| 3 | 59 |
| 4 | 66 |
| 5 | 72 |
| 6 | 76 |
| 7 | 80 |

In vitro dissolution studies were conducted on tablets prepared as described in Example 1. The dissolution method was the USP Paddle Method described in US Pharmacopoeia XXI (1985). The paddle speed was 100 rpm, the temperature was 37° C. and the media were USP Buffers (pH 1.6, 6.5 and 7.2).

Results are given in Table 4.

TABLE 4

| Time (hr) | wt % Hydromorphone released | | |
|---|---|---|---|
| | pH 1.6 | pH 6.5 | pH 7.2 |
| 1 | 34.7 | 36.0 | 36.6 |
| 2 | 48.1 | 51.2 | 51.0 |
| 3 | 58.5 | 61.7 | 61.1 |
| 4 | 66.5 | 70.0 | 69.8 |
| 6 | 79.1 | 81.8 | 81.8 |
| 8 | 88.2 | 90.6 | 90.7 |
| 10 | 95.1 | 97.7 | 99.2 |
| 12 | 100.0 | 100.0 | 100.0 |

Clinical Studies

A. A single dose, randomised, comparative, pharmacokinetic study was conducted on 4 subjects employing, (i) A hydromorphone hydrochloride tablet prepared as described in Example 1, (a 4 mg dose), and (ii) A normal release hydromorphone hydrochloride tablet (Dilaudid., Trade Mark; a 4 mg dose).

Analysis of the plasma samples for hydromorphone was performed by a double antibody radioimmunoassay. Plasma was assayed by incubating first with $^{125}$I-odohydromorphone and antimorphine antiserum (raised in oats against a 6-hemisuccinyl morphine-BSA conjugate), and subsequently with a solid phase bound antiserum suspension (Sac Cel. anti sheep/goat, Trade Mark). Following the addition of water the samples were centrifuged and the supernatant was removed. The radioactivity in the remaining pellet was counted on a multi-gamma counter for 60 seconds. Results are given in Table 5.

TABLE 5

| Time (hr) | Mean Plasma Conc. (ng/ml$^{-1}$) | |
|---|---|---|
| | Example 1 | Dilaudid |
| 0.50 | 0.9 | 9.4 |
| 1.0 | 3.8 | 8.8 |
| 1.50 | 4.4 | 8.6 |
| 2.0 | 4.2 | 7.8 |
| 2.5 | 4.5 | 7.9 |
| 3.0 | 4.8 | 6.2 |
| 4.0 | 4.3 | 3.5 |
| 6.0 | 3.0 | 3.2 |
| 8.0 | 1.4 | 1.6 |
| 10.0 | 1.6 | 1.0 |
| 12.0 | 1.0 | 0.5 |
| 24.0 | 1.1 | 0.5 |

B. A single dose, randomised, comparative, pharmacokinetic study was conducted on 12 subjects employing.

(i) A hydromorphone hydrochloride table prepared as described in Example 1 (a 4 mg dose), and '(ii) A normal release hydromorphone hydrochloride tablet (Dilaudid; Trade mark; a 4 mg dose).

Analysis of the plasma samples for hydromorphone was performed by the radioimmunoassay described in study A. Results are given in Table 6.

TABLE 6

| Time (hr) | Mean Plasma Conc. (ng/ml) | |
|---|---|---|
| | Example 1 | Dilaudid |
| 0.5 | 2.3 | 5.8 |
| 1.0 | 3.7 | 7.0 |
| 1.5 | 3.9 | 7.3 |
| 2.0 | 4.4 | 6.4 |
| 2.5 | 4.5 | 5.9 |
| 3.0 | 4.3 | 5.3 |
| 4.0 | 4.3 | 4.4 |
| 6.0 | 3.7 | 3.1 |
| 8.0 | 3.1 | 2.5 |
| 10.0 | 2.5 | 2.3 |
| 12.0 | 2.1 | 2.0 |
| 24.0 | 1.4 | 1.1 |

C. A single dose, comparative, pharmacokinetic study was conducted on 24 subjects employing, (i) A hydromorphone hydrochloride tablet prepared as described in Example 1 (a 4 mg dose) and, (ii) A normal release hydromorphone hydrochloride tablet (Dilaudid, Trade Mark, a 4 mg dose).

Analysis of the plasma samples for hydromorphone was performed and the results are given in table 7.

TABLE 7

| Time (hr) | Mean Plasma Concn. (ng/ml) | |
| --- | --- | --- |
| | Example 1 | Dilaudid |
| 0 | 0.12 | 0.15 |
| 0.5 | 0.57 | 2.68 |
| 1.0 | 0.67 | 2.23 |
| 1.5 | 0.74 | 1.78 |
| 2.0 | 0.75 | 1.47 |
| 2.5 | 0.72 | 1.11 |
| 3.0 | 0.69 | 0.94 |
| 3.5 | 0.65 | 0.82 |
| 4.0 | 0.59 | 0.77 |
| 5.0 | 0.71 | 0.53 |
| 6.0 | 0.59 | 0.40 |
| 8.0 | 0.40 | 0.29 |
| 10.0 | 0.49 | 0.26 |

What is claimed is:

1. A solid, controlled release, oral dosage form, the dosage form comprising a therapeutically effective amount of hydromorphone or a salt thereof in a matrix wherein the dissolution rate in vitro of the dosage form, when measured by the USP Paddle Method at 100 rpm at 900 ml aqueous buffer (pH between 1.6 and 7.2) at 37° C. is between 12.5% and 42.5% (by weight) hydromorphone released after 1 hour, between 25% and 55% (by weight) hydromorphone released after 2 hours, between 45% and 75% (by weight) hydromorphone released after 4 hours and between 55% and 85% (by weight) hydromorphone released after 6 hours, the in vitro release rate being independent of pH between pH 1.6 and 7.2 and chosen such that the peak plasma level of hydromorphone obtained in vivo occurs between 2 and 4 hours after administration of the dosage form.

2. A dosage form according to claim 1 wherein the in vitro dissolution rate is between 17.5% and 37.5% (by weight) hydromorphone released after 1 hour, between 30% and 50% (by weight) hydromorphone released after 2 hours, between 50% and 70% (by weight) hydromorphone released after 4 hours and between 60% and 80% (by weight) hydromorphone released after 6 hours.

3. A dosage form according to claim 2 wherein the in vitro dissolution rate is between 22.5% and 32.5% (by weight) hydromorphone released after 1 hour, between 35% and 45% (by weight) hydromorphone released after 2 hours, between 55% and 65% (by weight) hydromorphone released after 4 hours and between 65% and 75% (by weight) hydromorphone released after 6 hours.

4. A dosage form according to claim 1 wherein the peak plasma level of hydromorphone occurs between 2.25 and 3.75 hours after administration of the dosage form.

5. A dosage form according to claim 1 wherein a therapeutically effective amount of a hydromorphone salt comprises between 2 and 50 mg of hydromorphone hydrochloride.

6. A dosage form according to claim 5 wherein a therapeutically effective amount of a hydromorphone salt comprises between 2 and 40 mg of hydromorphone hydrochloride.

* * * * *

UNITED STATES PATENT AND TRADEMARK OFFICE
CERTIFICATE OF CORRECTION

PATENT NO. : 4,990,341
DATED : Issued February 5, 1991
INVENTOR(S) : Robert S. Goldie, et al.

It is certified that error appears in the above-identified patent and that said Letters Patent is hereby corrected as shown below:

ON THE TITLE PAGE:

"The portion of the term of this patent subsequent to Jul. 4, 2006 has been disclaimed."

should read:

--The term of this patent shall not extend beyond the expiration date of Patent No. 4,844,909.--

Signed and Sealed this

Thirtieth Day of January, 2001

*Attest:*

Q. TODD DICKINSON

*Attesting Officer*      *Director of Patents and Trademarks*